(12) United States Patent
Esfandyarpour et al.

US007932034B2

(10) Patent No.: US 7,932,034 B2
(45) Date of Patent: Apr. 26, 2011

(54) HEAT AND PH MEASUREMENT FOR SEQUENCING OF DNA

(75) Inventors: Hesaam Esfandyarpour, Stanford, CA (US); Mostafa Ronaghi, Los Altos Hills, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/959,317

(22) Filed: Dec. 18, 2007

(65) Prior Publication Data

US 2008/0166727 A1 Jul. 10, 2008

Related U.S. Application Data

(60) Provisional application No. 60/876,353, filed on Dec. 20, 2006.

(51) Int. Cl.
*C12Q 1/68* (2006.01)
*C12P 19/34* (2006.01)
(52) U.S. Cl. .......................... 435/6; 435/91.2
(58) Field of Classification Search .................. None
See application file for complete search history.

(56) References Cited

U.S. PATENT DOCUMENTS

| 4,237,224 | A | | 12/1980 | Cohen et al. |
|---|---|---|---|---|
| 4,863,849 | A | | 9/1989 | Melamede |
| 4,935,345 | A | | 6/1990 | Guilbeau et al. |
| 5,149,625 | A | | 9/1992 | Church et al. |
| 5,164,319 | A | | 11/1992 | Hafeman et al. |
| 5,252,743 | A | | 10/1993 | Barrett et al. |
| 5,302,509 | A | | 4/1994 | Cheeseman |
| 5,445,008 | A | | 8/1995 | Wachter et al. |
| 5,876,675 | A | | 3/1999 | Kennedy |
| 5,967,659 | A | | 10/1999 | Plotnikov |
| 6,048,498 | A | | 4/2000 | Kennedy |
| 6,055,002 | A | | 4/2000 | Wen et al. |
| 6,078,681 | A | * | 6/2000 | Silver ........................ 382/133 |
| 6,172,218 | B1 | | 1/2001 | Brenner |
| 6,192,939 | B1 | | 2/2001 | Yao et al. |
| 6,240,790 | B1 | | 6/2001 | Swedberg et al. |
| 6,284,113 | B1 | | 9/2001 | Bjornson et al. |
| 6,391,558 | B1 | | 5/2002 | Henkens et al. |
| 6,638,716 | B2 | | 10/2003 | Heller et al. |
| 6,780,591 | B2 | * | 8/2004 | Williams et al. ............... 435/6 |
| 6,953,958 | B2 | | 10/2005 | Baxter et al. |
| 7,141,370 | B2 | | 11/2006 | Hassibi et al. |
| 7,223,540 | B2 | | 5/2007 | Pourmand et al. |
| 2002/0123048 | A1 | | 9/2002 | Gau, Jr. |
| 2003/0008286 | A1 | * | 1/2003 | Zou et al. ..................... 435/6 |
| 2003/0106596 | A1 | | 6/2003 | Yang et al. |
| 2004/0142330 | A1 | | 7/2004 | Nyren et al. |
| 2004/0197793 | A1 | | 10/2004 | Hassibi et al. |
| 2005/0130173 | A1 | * | 6/2005 | Leamon et al. ............... 435/6 |
| 2006/0105373 | A1 | | 5/2006 | Pourmand et al. |
| 2006/0199193 | A1 | * | 9/2006 | Koo et al. .................... 435/6 |
| 2009/0127589 | A1 | | 5/2009 | Rothberg et al. |

FOREIGN PATENT DOCUMENTS

| WO | WO 9525815 A1 | * | 9/1995 |
|---|---|---|---|
| WO | 9813523 | | 4/1998 |
| WO | 9828440 | | 7/1998 |
| WO | 9967628 A1 | | 12/1999 |
| WO | 0043540 | | 7/2000 |
| WO | 0101025 A2 | | 1/2001 |
| WO | 0112327 A1 | | 2/2001 |
| WO | 0170400 A1 | | 9/2001 |

OTHER PUBLICATIONS

Purushothaman et al. Protons and single nucleotide polymorphism detection: A simple use for the Ion Sensitive Field Effect Transistor. Sensors and Actuators B (2006) 114: 964-968.*
Invitrogen Magnetic Separation Technology Brochure (2007) 8 pages.*
Jean G. Baillon, et al., "Continuous microspectrophotometric measurement of DNA polymerase activity: Application to the Klenow fragment of *Escherichia coli* DNA polymerase I and human immunodeficiency virus type 1 reverse transcriptase," Pro. Natl. Acad. Sci., USA, Feb. 1991, vol. 88, 1014-1018.
R. Bashir, et al., "Micromechanical cantilever as an ultrasensitive pH microsensor," Applied Physics Letters, Oct. 14, 2002, vol. 81, No. 16, 3091-3093.
Michael C. McAlpine, et al., "High-Performance Nanowire Electronics and Photonics on Glass and Plastic Substrates," Nano Letters, Oct. 14, 2003 (Web), vol. 3, No. 11, 1531-1535.
"LMC6001 Ultra Ultra-Low Input Current Amplifier," National Semiconductor, Dec. 2003.
Conceicao A.S.A. Minetti, et al., "The thermodynamics of template-directed DNA synthesis: Base insertion and extension enthalpies," PNAS, Dec. 9, 2003, vol. 100, No. 25, 14719-14724. H. Esfandyarpour, et al., "Geometrical Optimization of Pyrophosphate Concentration in Thermosequencing Platform for DNA Sequencing," COMSOL Conference, Mar. 14, 2007.
Hesaam Esfandyarpour, "A Picocalorimeter Assay for Label Free Gene Sequencing,[1]" Stanford Genome Technology Center, Center of Integrated Systems, Department of Electrical Engineering, Stanford University, NSTI—Nanotech 2007, 10th Annual Nanoscience and Technology Institute Conference, May 4, 2007.

(Continued)

*Primary Examiner* — Young J Kim
*Assistant Examiner* — Angela M Bertagna
(74) *Attorney, Agent, or Firm* — David J. Aston; Peters Verny, LLP

(57) ABSTRACT

The present method involves sequencing by synthesis in which a template strand having an attached primer is immobilized in a small volume reaction mixture. In one embodiment, the reaction mixture is in contact with a sensitive heat sensor, which detects the heat of reaction from incorporation of a complementary base (dNTP) in the presence of appropriate reagents (DNA polymerase, and polymerase reaction buffer). Alternatively, or in addition, a change in pH resulting from the incorporation of nucleotides in the DNA polymerase reaction is measured. A device is provided having delivery channels for appropriate reagents, including dNTPs, which may be delivered sequentially or in a mixture. Preferably, the dNTPs are added in a predetermined sequence, and the dNTP is incorporated or not depending on the template sequence.

18 Claims, 13 Drawing Sheets

OTHER PUBLICATIONS

Hesaam Esfandyarpour, "A Picocalorimeter Assay for Label Free Gene Sequencing, [2]" Stanford Genome Technology Center, Center of Integrated Systems, Department of Electrical Engineering, Stanford University, Biochemistry Conference, Fallen Leaf Lake, Oct. 4-6, 2006.

Hesaam Esfandyarpour, "ThermoSequencing: A Novel DNA Sequencing Method," Stanford Genome Technology Center, Center of Integrated Systems, Department of Electrical Engineering, Stanford University, Genetics Scientific Retreat, Monterey, CA, Sep. 20-22, 2006.

Marcel Margulies, et al., "Genome sequencing in microfabricated high-density picolitre reactors," Nature, Sep. 15, 2005, vol. 437, 376-380.

Nader Pourmand, et al., "Direct electrical detection of DNA synthesis," PNAS, Apr. 25, 2006, vol. 103, No. 17, 6466-6470.

Susan R. Mikkelsen, "Electrochemical Biosensors for DNA Sequence Detection," Electroanalysis, 1996, vol. 8, No. 1, 15-19.

* cited by examiner

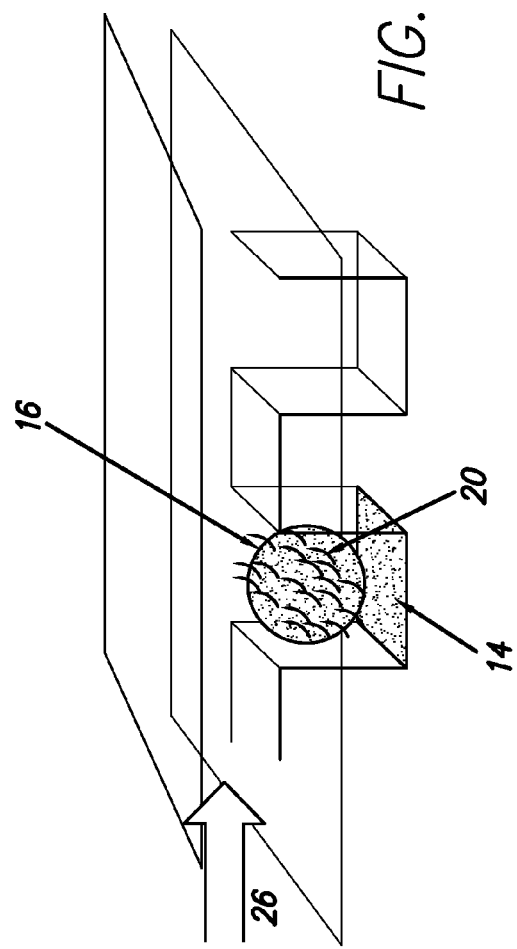
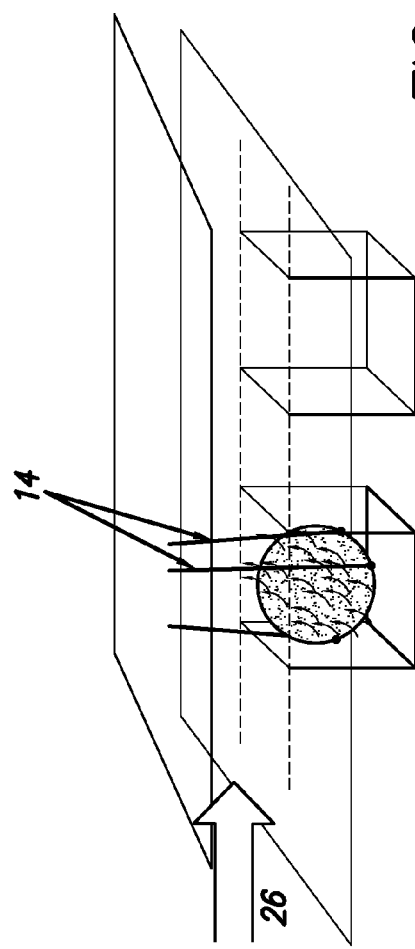

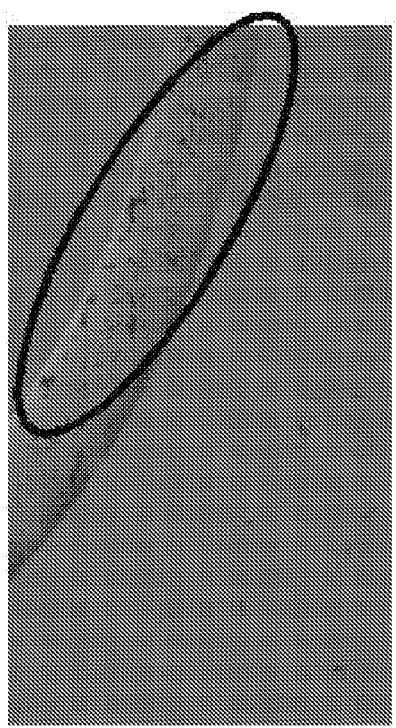
FIG. 2C
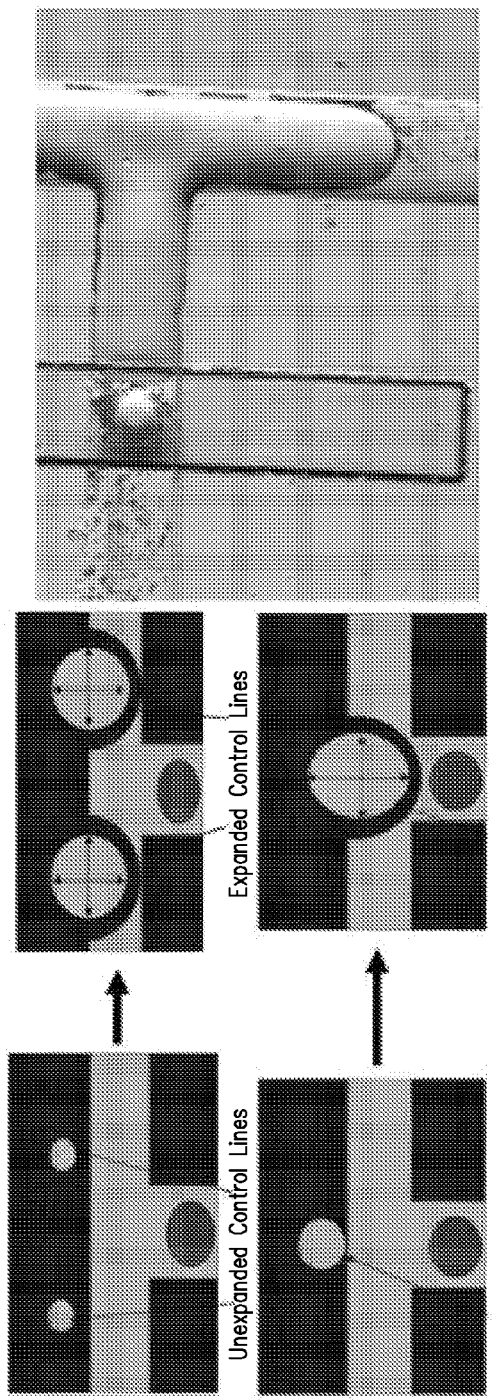
FIG. 2F
FIG. 2E
FIG. 2D

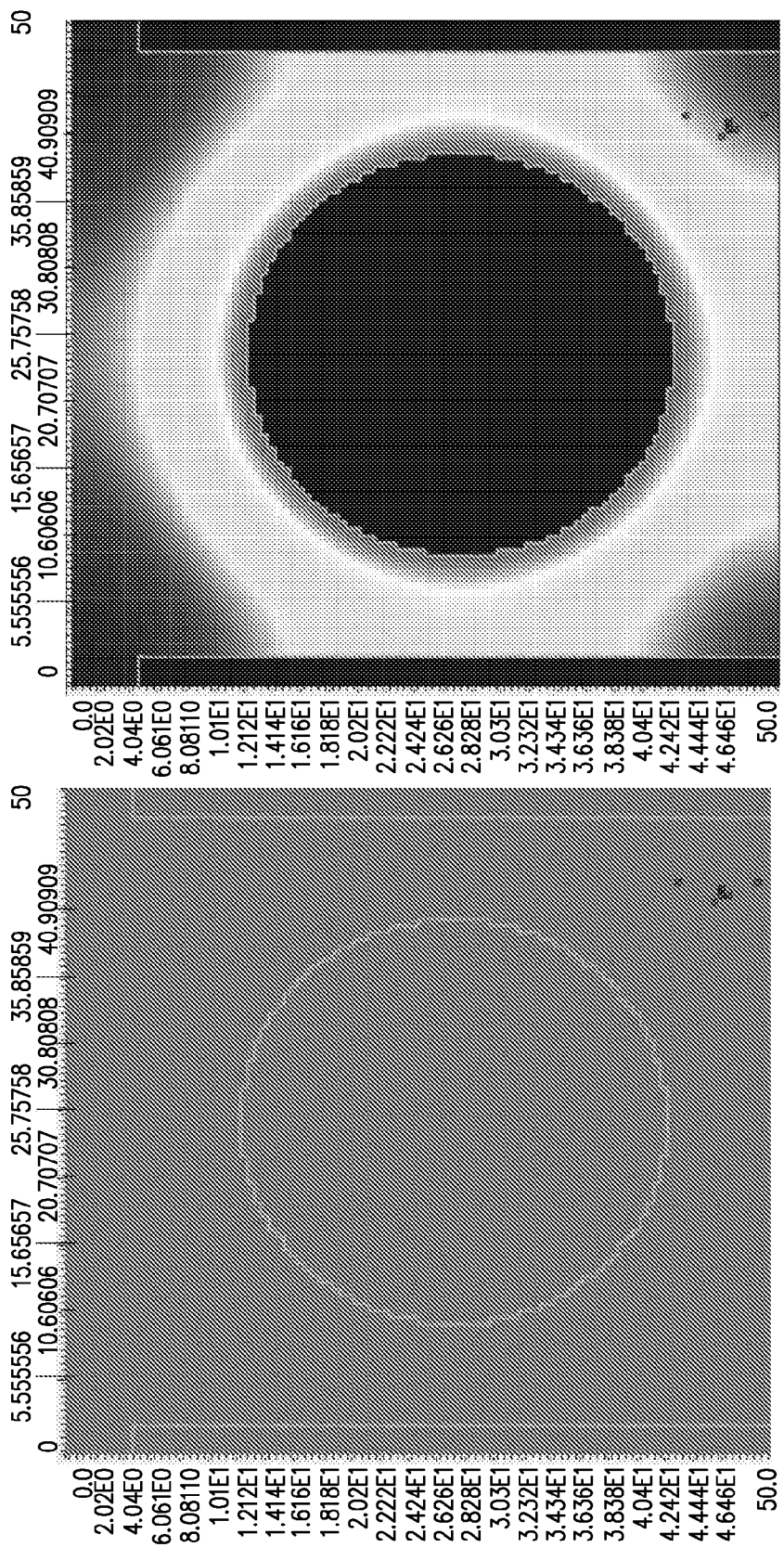

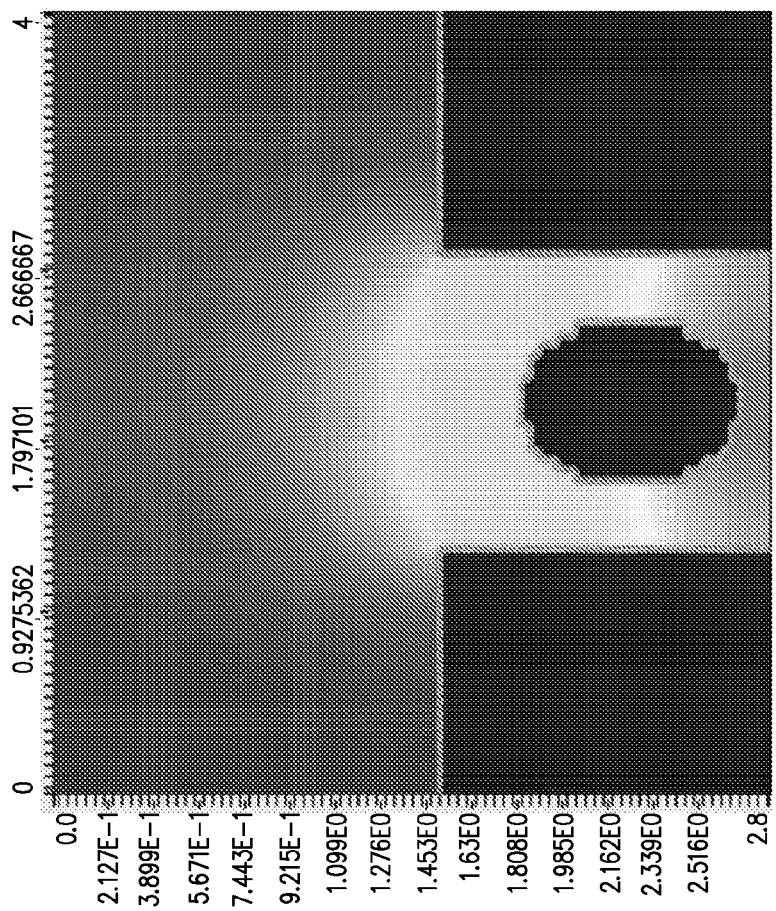
FIG. 4G  T=0s
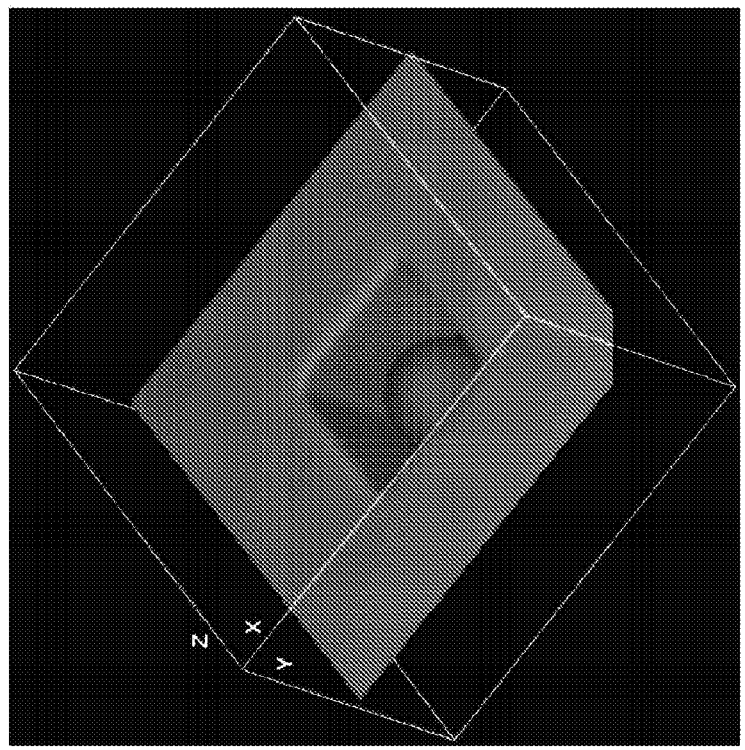
FIG. 4H  T=0.4s

HEAT AND PH MEASUREMENT FOR SEQUENCING OF DNA

CROSS-REFERENCE TO RELATED APPLICATIONS

This application claims priority from U.S. Provisional Patent Application No. 60/876,353 filed on Dec. 20, 2006, which is hereby incorporated by reference in its entirety.

STATEMENT OF GOVERNMENTAL SUPPORT

This invention was made with U.S. Government support under NIH Grant 1RO1HGO3571. The U.S. Government has certain rights in this invention.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer .txt file. Applicants incorporate the contents of the sequence listing by reference in its entirety.

BACKGROUND OF THE INVENTION

1. Field of the Invention

The present invention relates to the field of DNA sequencing and to the fields of calorimetry and potentiometry for chemical analysis.

2. Related Art

The essence of biology is a deep understanding of all of the species and their biological mechanisms. Speciation and biological function are primarily determined by the organism's DNA sequence. The development of vastly improved DNA sequence determination for personalized medicine and ecological studies could complete the revolution initiated by the Human Genome Project. The Human Genome Project was essentially accomplished by a reduction in the cost of DNA sequencing by three orders of magnitude. It is desired to reduce the cost by another three orders of magnitude to enable profiling of individuals genome. To achieve this goal, a highly integrated platform will be needed.

Current sequencing technologies involve a method of DNA sequencing known as sequencing by synthesis (SBS). See, for example, Seo et al. "Four-color DNA sequencing by synthesis on a chip using photocleavable fluorescent nucleotides," *PNAS* 102: 5926-5959 (Apr. 26, 2005). As described there, SBS was first introduced around 1988, See Hyman, "New method of sequencing DNA," *Anal. Biochem.*, 174: 423-436, (1 Nov. 1988). The method works by measuring pyrophosphate generated by the DNA polymerization reaction. DNA and DNA polymerase are held by a DEAE-Sepharose column and solutions containing different dNTPs are pumped through. The pyrophosphate generated is measured continuously by a device consisting of a series of columns containing enzymes covalently attached to Sepharose.

One approach to sequencing by detecting pyrophosphate is the pyrosequencing method, which is being commercialized by Biotage and 454 Life Sciences (a subsidiary of CuraGen Corp., Branford, Conn.).

Pyrosequencing is based on real-time bioluminometric detection of released pyrophosphate as a result of successful nucleotide incorporation. The released pyrophosphate is converted to ATP-by-ATP sulfurylase and the level of ATP is sensed by a luciferase producing proportional light signal, which is detected by photosensing devices. Biotage is performing this assay in 96 well format and 454 Life Sciences perform the reaction in picotiter plate format for analysis of more than 100,000 DNA fragments simultaneously.

Pyrosequencing is further described in Ronaghi, M., Uhlen, M., and Nyren, P. 1998, *Science* 281: 363, "A sequencing method based on real-time pyrophosphate." 454's technology is based on performing hundreds of thousands of simultaneous sequencing reactions in small volume wells on plates. All molecular biology reactions—DNA amplification, sequencing by synthesis, and signal light generation—occur in a single well.

An extension of the original "fluorescent in situ sequencing," termed bead-based polony sequencing, was developed by Jay Shendure and colleagues in George Church's Lab at the Lipper Center for Computational Genetics, Harvard Medical School, Boston. In this sequencing-by-synthesis approach, short fragment DNA libraries are clonally amplified onto 1-μm beads and embedded into a polymer matrix on the surface of microscope slides. The polony slides are then placed into an automated flow cell, where four-color, fluorescently labeled reagents (corresponding to the DNA bases, A, C, G, or T) are delivered to serially sequenced DNA strands.

Other DNA sequencing methods have been proposed. One approach to generating paired genome-fragment tags uses an emulsion PCR-based amplification step, an optimized polymerase colony (polony)-based sequencing-by-ligation protocol and a conventional epifluorescence microscope with a sophisticated algorithm that allows researchers to stitch together the fragmented sequence reads into one continuous thread. See *Science* 309, 1728-1732, 2005.

Specific Patents and Publications

Wang et al., "Continuous Flow Thermal Cycler Microchip for DNA Cycle Sequencing," *Anal. Chem.*, 78 (17), 6223-6231, 2006, discloses a polymer-based continuous flow thermal cycler (CFTC) microchip for Sanger cycle sequencing using dye terminator chemistry. The CFTC chip consisted of a 20-loop spiral microfluidic channel hot-embossed into polycarbonate (PC) that had three well-defined temperature zones poised at 95, 55, and 60° C. for denaturation, renaturation, and DNA extension, respectively.

U.S. Pat. No. 5,149,625 to Church, et al., issued Sep. 22, 1992, entitled "Multiplex analysis of DNA," discloses a method including the steps of: a) ligating the DNA into a vector comprising a tag sequence, the tag sequence having at least 15 bases, wherein the tag sequence will not hybridize to the DNA under stringent hybridization conditions and is unique in the vector, to form a hybrid vector, b) treating the hybrid vector in a plurality of vessels to produce fragments comprising the tag sequence, wherein the fragments differ in length and terminate at a fixed known base or bases, wherein the fixed known base or bases differs in each vessel, c) separating the fragments from each vessel according to their size, d) hybridizing the fragments with an oligonucleotide able to hybridize specifically with the tag sequence, and e) detecting the pattern of hybridization of the tag sequence, wherein the pattern reflects the nucleotide sequence of the DNA.

U.S. Pat. No. 4,863,849 to Melamede, issued Sep. 5, 1989, entitled "Automatable process for sequencing nucleotide," discloses a sequencing by synthesis method which involves adding an activated nucleotide precursor (a nucleoside 5'-triphosphate) having a known nitrogenous base to a reaction mixture comprising a primed single-stranded nucleotide template to be sequenced and a template-directed polymerase. The reaction conditions are adjusted to allow incorporation of the nucleotide precursor only if it is complementary to the single-stranded template at the site located one nucleotide residue beyond the 3' terminus of the primer. After allowing sufficient time for the reaction to occur, the reaction mixture is washed so that unincorporated precursors are removed while the primed template and polymerase are retained in the reaction mixture.

U.S. Pat. No. 5,302,509 to Cheeseman, issued Apr. 12, 1994, entitled "Method for sequencing polynucleotides," discloses a method for determining the sequence of nucleotides on a single strand DNA molecule. The single strand DNA molecule is attached to a leader oligonucleotide and its complementary strand to a solid-state support. Fluorescently labeled 3'-blocked nucleotide triphosphates, with each of the bases A, G, C, T having a different fluorescent label, are mixed with the bound DNA molecule in the presence of DNA polymerase.

US 2004/0142330 to Nyren, et al., published Jul. 22, 2004, entitled "Method of sequencing DNA," discloses a method of pyrosequencing which use an α-thio analogue of deoxy ATP (dATP) (or dideoxy ATP (ddATP)) namely an (1-thio) triphosphate (or α-thiophosphate) analogue of deoxy or dideoxy ATP, preferably deoxyadenosine[1-thio]triphosphate. Use of these modified analogues is an improvement to the basic PPi-based sequencing method in which one uses in place of dATP, a dATP analogue (specifically dATP α-s) which is incapable of acting as a substrate for luciferase, but which is nonetheless capable of being incorporated into a nucleotide chain by a polymerase enzyme (WO98/13523).

Further improvements to the basic PPi-based sequencing technique include the use of a nucleotide degrading enzyme such as apyrase during the polymerase step, so that unincorporated nucleotides are degraded, as described in WO 98/28440, and the use of a single-stranded nucleic acid binding protein in the reaction mixture after annealing of the primers to the template, which has been found to have a beneficial effect in reducing the number of false signals, as described in WO00/43540.

US 2003/0082583 by Hassibi, et al., published May 1, 2003, entitled "Bioluminescence regenerative cycle (BRC) for nucleic acid quantification," discloses another technique that employs pyrophosphate. In BRC, steady state levels of bioluminescence result from processes that produce pyrophosphate. Pyrophosphate reacts with APS in the presence of ATP sulfurylase to produce ATP. The ATP reacts with luciferin in a luciferase-catalyzed reaction, producing light and regenerating pyrophosphate. The pyrophosphate is recycled to produce ATP and the regenerative cycle continues.

Another, different, reaction sensor is disclosed in U.S. Pat. No. 6,638,716 to Heller, et al., issued Oct. 28, 2003, entitled "Rapid amperometric verification of PCR amplification of DNA." This device utilizes an electrode coated with a redox polymer film. The redox polymer film is preferably a redox hydrogel. A binding agent is immobilized in the redox polymer film, preferably through covalent bonding of the binding agent to the redox polymer. The DNA is labeled, while amplified, with two or more different ligands, the first of which binds strongly to the binding agent immobilized in the redox polymer film. When the sample in which the amplification is to be confirmed is contacted with the electrode, amplified DNA is immobilized on the electrode through linkage of the immobilized binding agent in the redox polymer film with the first ligand. The presence of the amplified DNA on the electrode is detected through exposure of the electrode to a detection marker. The detection marker is a molecule with two functional groups. One of the functional groups binds with the second ligand of the amplified DNA; the second functional group of the detection marker produces an electrochemically detectable signal.

BRIEF SUMMARY OF THE INVENTION

The following brief summary is not intended to include all features and aspects of the present invention, nor does it imply that the invention must include all features and aspects discussed in this summary.

Described is a new technique based on sequencing-by-synthesis, which has the potential to reduce the cost of genome sequencing. The described method relies on heat, IR and/or pH detection resulting from DNA synthesis.

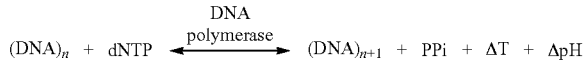

$$(DNA)_n + dNTP \xrightleftharpoons{\text{DNA polymerase}} (DNA)_{n+1} + PPi + \Delta T + \Delta pH$$

The physical reaction products are shown in bold in the formula above. The formula represents the incorporation of a nucleotide, dNTp, which could be any nucleotide, G: Guanine, A: Adenine; T: Thymine, or C: Cytosine as incorporated into a growing DNA strand. The T in the above reaction is about 22 kT or ~570 meV per nucleotide incorporation, and is measured in accordance with the present invention, as well as ΔpH.

The incorporation of the nucleotide in the above reaction is monitored, by monitoring changes in heat or pH, to provide sequence information.

The present invention is directed to sequencing using template dependent DNA synthesis. As is known in this process, an enzyme called DNA polymerase binds to the DNA to be replicated and synthesizes DNA from a primer, which is RNA in cellular division, but which may be RNA or DNA here. This primer indicates the starting point for the elongation. DNA polymerases can only synthesize the new DNA in the 5' to 3' direction.

In certain aspects, the present invention comprises a method for sequencing a single stranded DNA template, which comprises the step of providing a primer region of the DNA template. The primer region may be a hairpin turn of a single strand, which hybridizes to itself, or it may be a specific primer added to the reaction mixture. The template DNA is placed in a reaction well having a fluid volume of less than about 0.1 uL. The small volume size of the reaction chamber, and the small fluid volume of the reactants are chosen to facilitate the measurement of heat and/or pH, which changes may be difficult to measure when dissipated in a large volume. One adds to the reaction well a DNA polymerization mixture containing DNA polymerase and a plurality of nucleotides, as is known in the art. Then, the method comprises the step of measuring one or both of a pH change of at least about 0.001 units (up to about 0.3 units) and a temperature change of at least about 0.003° C., whereby incorporation of the nucleotides produces heat or pH change indicative of a sequence of the DNA template. The volumes used and the pH units and temperatures measured will be determined by practicalities of instrument sensitivity. In certain aspects, the reaction volume should be less than about 70 pL ($10^{-12}$ L) down to about 30 fL ($10^{-15}$ L). The method is preferably carried out in a controlled environment as to temperature, outside moisture, etc.

The present invention also comprises devices for implementing the present heat and/or pH based sequencing methods. These devices comprise a microfluidic device, i.e., one that can deliver in controlled fashion small volumes of reactants. The devices may comprise a plurality of wells for reactants, and be configured for massively parallel reactions. The present reaction wells will be adapted and arranged to contain a pH sensor and/or a heat sensor in the reaction well. The heat sensor is preferably an infrared sensor. These sensors are sensitive to very small pH and heat changes. The preferred pH sensor of the present device is one that can detect a change of at least about 0.3 and down to about 0.001 pH units. The temperature sensor of the present device can detect a change of at least about 0.003° C. The sensor may be a picocalorimeter, a thermocouple, a thermometer, or an IR sensor. The sensor may be arrayed adjacent to or inside the reaction well, and may be planar so as to present a more exposed area in the small reaction volume. The microfluidics platform preferably comprises a heat insulating material, such as polydimethyl siloxane (PDMS). The microfluidic platform also preferably contains lines for delivering the reactants into and out of the reaction wells, and control lines for sealing the reaction wells during NTP incorporation and heat/pH changes. When the reaction well is sealed, a fluid is pumped into a control line so that it expands radially to a size larger than the reaction well opening. It has been found that a single control line sealing a well is superior to multiple lines.

BRIEF DESCRIPTION OF THE DRAWINGS

FIG. 2 is a schematic diagram showing a microfluidics path and sensor arrays for a sequencing bead (A): a microphotograph of magnetic beads in a PDMS channel (B); and a PDMS microfluidic system (C); 2D shows a diagram of expandable control lines adjacent to a bead in a reaction well, with a dual line embodiment (top) and a single line embodiment (bottom) prior to expansion of the control lines; 2E shows the control lines of FIG. 2D in open position; and 2F is a micrograph showing a dual control line embodiment in a PDMS microfluidic device with numerous paramagnetic beads visible;

FIG. 4A-H is a series of computer simulated heat generation profiles at various times as indicated in A-F, with, at bottom left (G) a side view of the bead in its well, and a perspective view (H) of the bead as modeled in that simulation;

DETAILED DESCRIPTION OF THE PREFERRED EMBODIMENT

Overview

Figure 1A:
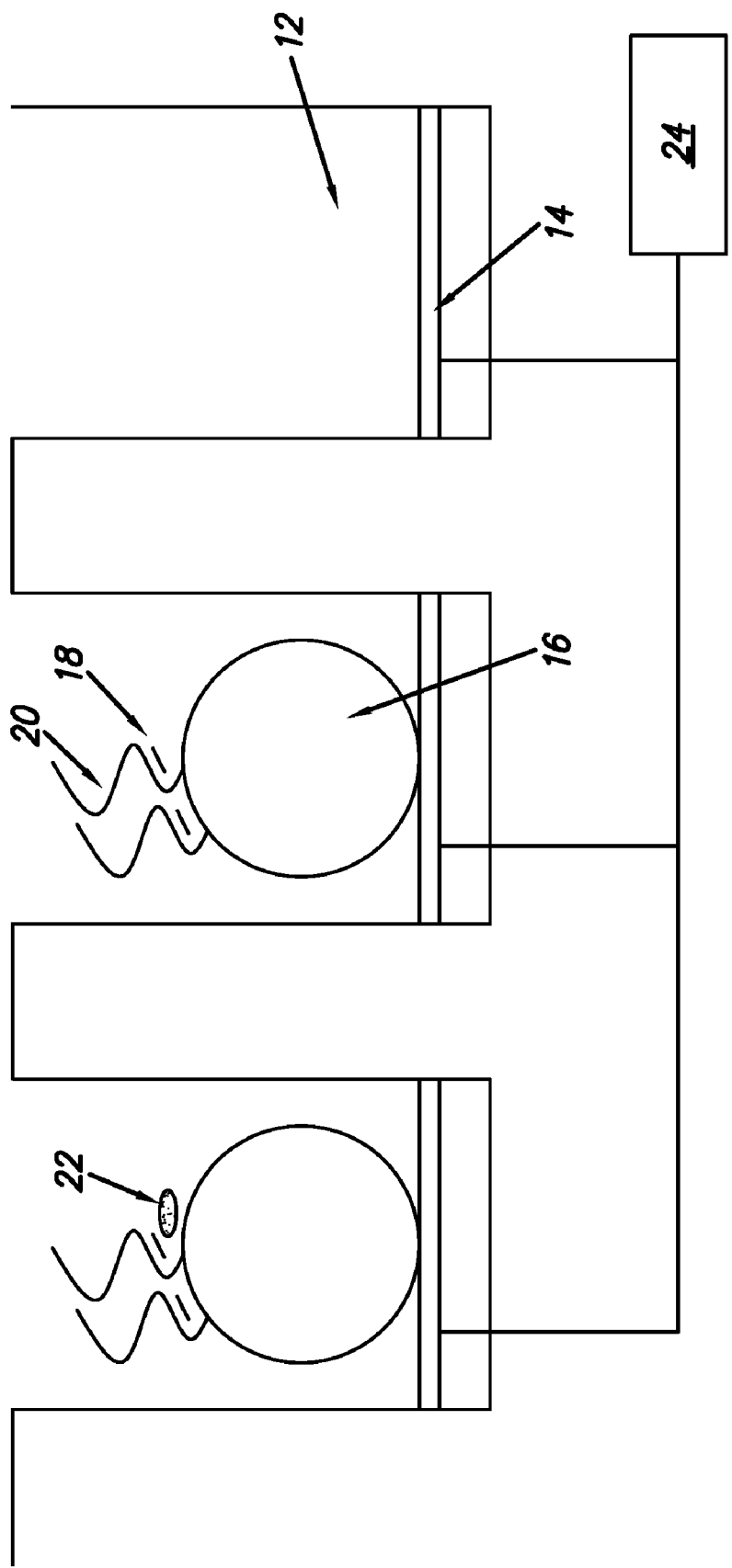
FIG. 1A is a schematic representation of a bead-based sequencing method in which pH and/or temperature is monitored.
Figure 1B:
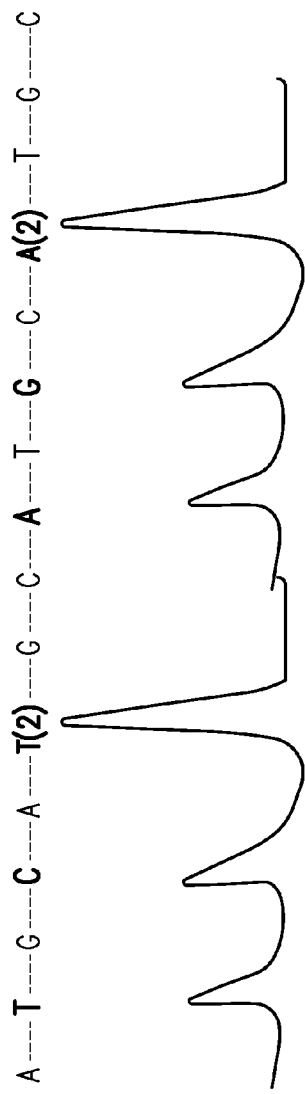
FIG. 1B shows a schematic view of a sequence as obtainable with the present methods and device (SEQ ID NO: 2)
Figure 1C:
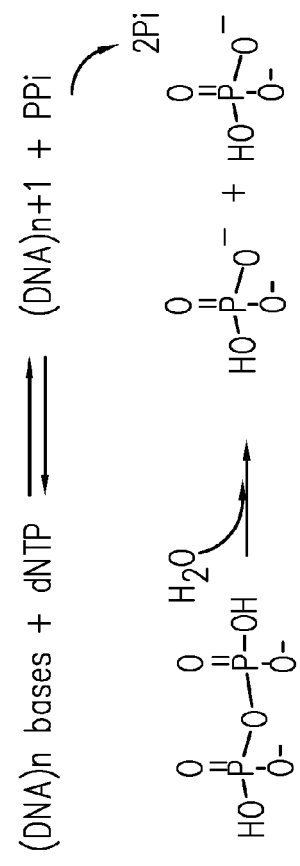
FIG. 1C shows a reaction of DNA incorporation.

The present method involves a method of sequencing by synthesis (SBS) in which a template strand having an attached primer is immobilized in a small volume reaction mixture, with the reaction mixture in contact with a sensitive calorimeter, which detects the heat of reaction from incorporation of a complementary base (dNTP) in the presence of appropriate reagents (DNA polymerase, and polymerase reaction buffer) (see FIG. 1C). Alternatively, a pH meter may be used to measure changes in pH resulting from the reaction. The bead will have template DNA attached to it, where the sequence of the template DNA molecule is the same in each of numerous strands attached to the bead, though biotin. In a known protocol, for example, 5 pg of immobilized template DNA is used. The template DNA is prepared with a known segment, for attachment of a primer. No dyes, labels or artificial chain termination is required in the present method.

As can be seen from FIG. 1C, DNA polymerization results in an increased negative charge in the solution generated by released pyrophosphate (PPi) and inorganic phosphate (Pi). FIG. 1C also illustrates the splitting of PPi to 2 Pi. This can be accomplished with addition of pyrophosphatase, and will further generate heat and H+ (lowered pH) for measurement in the present method. Other enzymes such as ATPase and ATP sulfurylase may be used to increase PPi and resultant temperature and pH changes. A non-aqueous solvent can be used to reduce pH interference from $H_2O$.

The present method may be used to obtain relatively short sequence reads, e.g., sequence reads about 80-120 bases long, at 96% average accuracy in a single run. One may use Phred 20 as a cutoff to determine read accuracy, see Margulies, "Genome sequencing in microfabricated high-density picolitre reactors," *Nature* 437, 376-380 (15 Sep. 2005). A large number of sequence reads may be obtained in parallel, e.g., with thousands of reaction wells, and/or multiple reactions per well. Generally, as is described in detail below, beads or other discrete particles are placed in wells, which are arranged and sized so that no more than one bead may be present in a well at a single time.

The small volume reaction chamber, or micro-cell, contains, in a preferred embodiment, a DNA-bead complex as shown in FIG. 1A and FIG. 2. FIG. 1A illustrates a bead based SBS method according to the present invention. Reaction wells 12 contain no more than one bead 16 each. The well is sized so that a bead diameter is more than half of the diameter of the well reaction opening, to prevent more than one bead from entering a well. The wells each contain a sensor 14, which measures heat and/or pH. A bead 16 has immobilized on its surface a number of single DNA strands 20, to which have been hybridized primer sequences 18 complementary to the strand 20 whose sequence is to be determined. The primers may also be provided by a hairpin configuration of strand 20. To carry out a DNA polymerization, DNA polymerase 22 is added to a reaction solution in which is immersed the beads and DNA, along with buffers and cofactors, and a number of molecules of a single species of dNTP (A, T, G or G). If the dNTP (e.g., A) is complementary to the next base in strand 20 after the template 18, the dNTP is incorporated and heat and H+ are given off. Individual wells and sensors are separated by a thermally insulating material so that temperature increases in individual wells can be measured. If no binding occurs, the dNTP is removed through washing, and another preselected dNTP (e.g., T) is added. The heat/pH are measured by a sensitive instrument 24.

The nucleotide additions and washing steps result in an instrument read out as shown in FIG. 1B. There, one sees pre-selected addition of bases in the arbitrary sequence A, T, G, and C (SEQ ID NO: 2 shown in Figure), with peaks of increase in temperature and/or decrease in pH occurring for the sequence TCTTAGAA. In contrast, addition of non-complimentary bases shows no peak, such as with the first added A.

To scale the technology to high-throughput format, the present device preferably further comprises a flow-based array system to carry reagents to an array of micro-cells containing immobilized DNA. The heat, IR and/or pH generated from DNA synthesis reaction is detected by having a probe in proximity to the reaction. The detection device is preferably a part of, or in, the well where the DNA sequencing reaction takes place. Fabrication of an array comprising millions of wells equipped with probes can be envisioned.

FIG. 2A shows an example of a microfluidic device where a bead containing numerous template strands of DNA is in a reaction well. Nucleotides and reagents are flowed through a channel in the microfluidics device to the reaction well containing the template bearing bead. The well may be formed from etched silicon, with a glass cover slip as a seal over the well and channels. A sensor at the bottom of the well, in proximity to the bead, measures temperature/pH changes. The sensor may also take the form shown in the lower panel of FIG. 2A, namely a number (e.g., three) of wire-like probes inserted into the well in the vicinity of the bead. For IR detection, one may use a thin film IR detector or a photodiode. For temperature detection independent of IR, one may use a thermocouple that is micro-etched or formed from adjacent nanowires. For pH detection, the probes may be microcantilevers sensitive to H+ concentration, as described below, or other pH sensors.

In order to maximize well coverage efficiency by beads, one may use magnetic beads and drive the beads to the well by applying a magnetic field.

Calorimetric measurement is preferred as providing the most sensitive detection schemes. Very sensitive detection allows detection of different heat signatures for different nucleotides. As a result, each well may contain a mixture of nucleotides, or 16 possible dinucleotides, e.g., AT, AG, AC, AA, TA, TG, TC, TT, etc. A unique signature is generated by the incorporation of the growing chain of the appropriate nucleotide. This allows synthesizing by synthesis, measuring the heat and/or pH changes generated by the above-described reactions, where the sequence is associated with a unique peak identifiable by its size and/or shape.

Figures 4C, 4D:
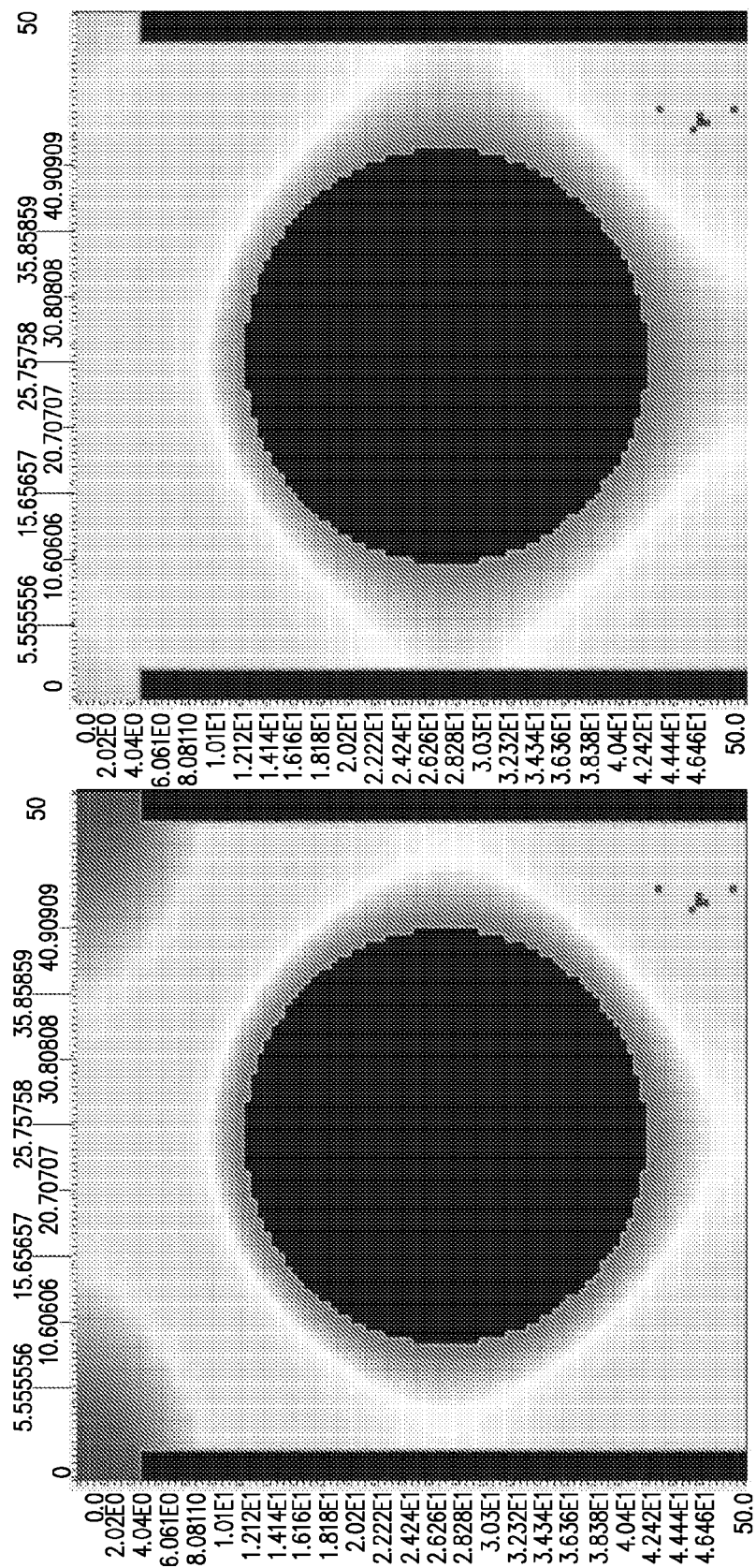
Figure 4F:
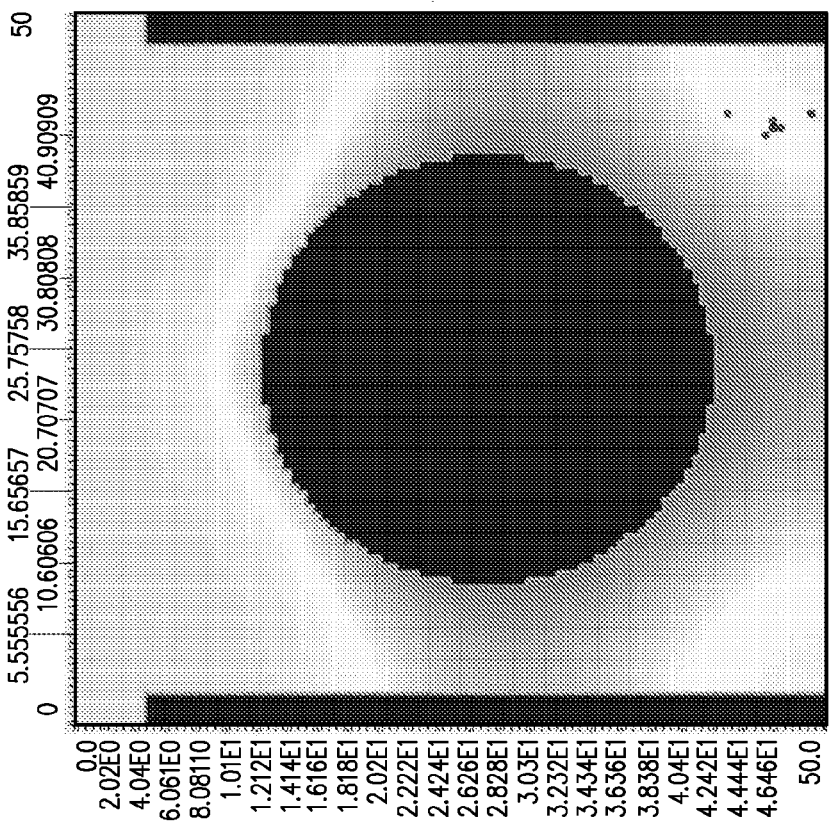

The geometry and amount of DNA needed to have detectable DNA synthesis (heat generation profile is demonstrated on the left), is illustrated at the bottom of FIG. 4. That is, it can be seen that, over the time course illustrated in A through &, the spread of heat from the bead is not radially uniform, creating a region of greater heat. As can be seen in FIG. 4F and in the side view of FIG. 4G, the heat is transmitted more to the bottom of the well, making the placement of a heat sensor at the bottom portion of the well, e.g., the bottom surface, advantageous.

The microfluidics platform preferably contains an array of wells and sensors, and channels for delivering reagents to the wells. The device preferably has channels at least some of which are less than 1 nm in diameter. Pressure or electroosmotic pumping may be used to drive the fluids and reactants through the channels. If the walls of a microchannel have an electric charge, as most surfaces do, an electric double layer of counter ions will form at the walls. When an electric field is applied across the channel, the ions in the double layer move towards the electrode of opposite polarity. This creates motion of the fluid near the walls and transfers via viscous forces into convective motion of the bulk fluid. If the channel is open at the electrodes, as is most often the case, the velocity profile is uniform across the entire width of the channel.

PDMS (polydimethylsiloxane) microfluidic chips (see, e.g., FIGS. 2B and 2C) with integrated micromechanical valves can be built using soft lithography as described previously (Unger, M. A., Chou, H—P, Thorsen, T., Scherer, A. and Quake, S. R. (2000) Monolithic microfabricated valves and pumps by multilayer soft lithography, *Science,* 288, 113-116, and Kartalov et al., "Microfluidic device reads up to four consecutive base pairs in DNA sequencing-by-synthesis," *Nucleic Acids Research,* 2004, Vol. 32, No. 92873-2879). Further guidance on a microfluidics DNA sequencing device may be found in Margulies, et al. "Genome Sequencing in Open Microfabricated High Density Picoliter Reactors," *Nature,* 2005 Sep. 15; 437(7057): 376-380. Such a device, as described there, uses a novel 60×60 mm$^2$ fiber optic slide containing 1,600,000 individual wells. To provide sequencing templates, one may clonally amplify DNA fragments on beads in the droplets of an emulsion. The template-carrying beads are loaded into the wells to convert each into a picoliter-scale sequencing reactor. One then performs sequencing by synthesis using the present protocols.

A pico-calorimetric sensor may be micro-fabricated in a flow-based array of wells so that each is equipped with a pico-calorimeter for DNA sequencing. Alternatively, each well may be equipped with a thin film IR detector or a photodiode. For temperature detection independent of IR, each well may be equipped with a thermocouple, which is micro-etched or formed from adjacent nanowires. For pH detection, each well may be equipped with a microcantilever sensitive to H+ concentration, such as is described in Bashir et al., "Micromechanical cantilever as an ultrasensitive pH sensor", *Applied Physics Letters,* 81:16, 14 Oct. 2002, pp. 3091-3093. In addition, other applications of this system will be apparent.

Each well containing reactants and beads is thermally isolated from other reaction wells. This may be accomplished, for example, by having empty wells on either side of experimental wells. Alternatively, a control channel may be situated on top of each reaction well. Other methods may also be used, such as using thermally insulating materials to define the wells. This will prevent heat signatures from one well from interfering with another reaction detection.

The injection system must sequentially introduce and remove dNTPs and other reactants in a stable and uniform injection system. The system may sequentially analyze individual dNTP binding, or may be used with a mixture of nucleotides (dNTPs) in a run-off process. The effect of dilution resulting from the addition of different reactants may be calculated according to known methods. (See, Minetti et al., above). Their results reveal exothermic heats between −9.8 and −16.0 kcal/bp for template-directed enzymatic polymerization. These extension enthalpies depend on the identity of the inserting base, the primer terminus, and/or the preceding base.

Background noise and noise due to injection fluctuation can be adjusted by use of known standards in calibrating sequencing. The present methods and devices may be developed for uses where long read lengths and high accuracy scores are not needed, e.g., pathogen screening. For purposes of calibration and/or normalizing data, non-natural bases may be added for incorporation by the polymerase. See, Tan et al., Kinetic analysis of the Coding Properties of O$^6$-Methylguanine in DNA: the Crucial Role of the Conformation of the Phosphodiester Bond," *Biochem.* 33:5335-5346 (1994).

The microfluidic device to be used to deliver buffer, DNA polymerase, nucleotides (ATP, TTP, GTP, CTP) and, optionally, to deliver oligonucleotides to be delivered and hybridized to the immobilized DNA template will preferably involve a number of channels leading to and from the reaction wells. In addition, a mixing chamber may be fabricated to allow premixing of the reagents prior to introduction in the reaction well. A microfluidic mixing chamber is described in US 2003/0106596 to Yang, et al., published Jun. 12, 2003, entitled "Microfluidic system for controlled fluid mixing and delivery." Microfluidic systems adaptable for the present device are used in several applications. For example, U.S. Pat. No. 5,445,008 discloses these systems in biomedical research such as DNA or peptide sequencing. U.S. Pat. No. 4,237,224 discloses such systems used in clinical diagnostics such as blood or plasma analysis. U.S. Pat. No. 5,252,743 discloses such systems used in combinatorial chemical synthesis for drug discovery. U.S. Pat. No. 6,055,002 also discloses such systems for use in ink jet printing technology.

The so-called "Lab-on-a-Chip" generally refers to a microfabricated device of microfluidic systems that regulate, transport, mix and store minute quantities of liquids rapidly and reliably to carry out desired physical, chemical, and biochemical reactions in larger numbers. Those devices have been disclosed in U.S. Pat. No. 5,876,675, U.S. Pat. No. 6,048,498, and U.S. Pat. No. 6,240,790 and European WO 01/70400. One of the most important issues in the lab-on-a-chip devices is the moving and mixing of multiple transport fluids inside the chip in a controlled fashion. Several methods of transferring and controlling of liquids have been disclosed by U.S. Pat. No. 6,192,939 and U.S. Pat. No. 6,284,113 and by European WO 01/01025 and WO 01/12327. However, those methods involve either electrokinetic transport mechanisms or controlling applied pressure or vacuum.

Overall, the present method uses label-free dNTPs and only one enzyme, DNA polymerase. It is not necessary to add additional enzymes such as apyrase in order to eliminate unwanted signal. In addition, various designs for sensitive thermocouples and temperature sensors may be implemented by low cost fabrication techniques, as described below. Numerous different sequencing reactions may be carried out in parallel in a microfluidics device having different reaction wells, each containing different templates and primers.

Preparation of Samples

Each bead preferably has attached to it numerous strands of ~1 kb of ssDNA, based on expected read lengths of 100-200 base pairs. For example, in an SNP project, one could start with a cheek swab, then, using specific primers, amplify up the genomic regions in which one wishes to sequence SNP makers. Additional specifics on a suitable bead preparation may be found in U.S. Pat. No. 6,172,218 to Brenner, issued Jan. 9, 2001, entitled "Oligonucleotide tags for sorting and identification." This patent describes a method for directing beads to specific reaction wells through tagging.

Magnetic beads may be used, such as are described in Kojima et al., "PCR amplification from single DNA molecules on magnetic beads in emulsion: application for high-throughput screening of transcription factor targets," *Nucleic Acids Res.* 2005; 33(17): e150. This protocol uses a magnetic bead solution (100 µl) (Dynabeads M-270 carboxylic acid, 2.8±0.2 µm in diameter, Dynal Biotech, Lake Success, N.Y.). The present beads may vary in size, e.g., 1-2 µM for magnetic beads, or ~30 mM (e.g., (e.g., 28 µM) for sepharose (agarose) beads.

Each bead preferably contains a population (at least about $10^3$, preferably at least $10^6$) of essentially identical polynucleotides for which sequence information is desired. The polynucleotides (i.e., multiple copies of template DNA) are preferably formed from an initial sample by an amplification process, which will produce multiple identical copies of the polynucleotide, such as PCR. Both the ssDNA template and the added nucleotides may be unlabeled. Microparticle supports further include commercially available nucleoside-derivatized CPG and polystyrene beads available from Applied Biosystems, Foster City, Calif.); derivatized magnetic beads; polystyrene grafted with polyethylene glycol (e.g., Tenta-Gel™, beads Rapp Polymere, Tubingen Germany); and the like. Selection of the support characteristics, such as material, porosity, size, shape, and the like will apparent to those skilled in the art.

Thus, a number of beads, 16 preferably, have immobilized thereon multiple DNA strands 14, which have the same sequence to be determined. The DNA strands are attached at their 3' ends, and may contain linker or adapter sequences. A primer is then allowed to anneal to the DNA template in the vicinity of the 3' end. This duplex will be extended away from the surface of the bead in the case of DNA polymerization as new nucleotides (dNTPs) are added to the primer. The beads so prepared are delivered to small volume cells (reaction wells 12) to allow sensitive heat/IR or PH detection.

Preparation of Microfluidic System

FIG. 2A, as described above, shows a bead in a reaction well, with a sensor 14, which is comprised in a microfluidic system. The arrow represents flow through a microfluidic channel in a solid substrate, into which nucleotides 26 are being added to flow into a well having a single bead 16 with numerous identical template strands attached. The microfluidic system may be made of any material which is known for fabrication of reaction areas, channels, valves and the like, such as silicon, glass, plastic polymers. Polymers that do not conduct heat are preferred, such as PDMS. Other polymers may be used, with insulating materials disposed between the wells and the temperature sensors. In FIG. 2B, the sensors are probes inserted into the well, rather than a planar sensor at the bottom of the well.

FIGS. 2C and 2F are a pair of micrographs showing magnetic beads in a channel in a PDMS microfluidic system. The beads were injected into a pre-formed channel. In the present device, the DNA to be sequenced may be directly immobilized in the reaction well, but it does not need to be, as is in the case of other sequencing techniques. In the present device, the template DNA does not need to be directly connected to the sensor that detects the sequencing reaction. In certain embodiments, it is preferable to connect the DNA template strands to a moveable particle, such as a bead, which can be transported and delivered into reaction areas where the reagents are added and the resultant temperature and H+ increase is measured. In the lower micrograph, FIG. 2F, a small enlargement in the fluid channel may be seen, which may serve as a reaction well. This shows a double-control line system for a 100 µm wide channel. In FIG. 2F, dark lines surrounding the reaction well are control lines for trapping fluid and reactants in the well. As shown in FIGS. 2D and 2E top, and illustrated in FIG. 2F, a sketch of a microfluidic device may be designed with a control line on either side of the reaction area. A more preferred device is shown in FIGS. 2D and 2E bottom, where a single control line is used.

Expansion of this control line both stops the fluid flow in or out of the reaction area, and serves to block the depression which serves as the reaction area, thereby effectively reducing the volume of the reaction area and better insulating the area, causing it to retain more heat for detection. The control line may be fabricated from an elastomeric material such as PDMS, silicone rubber, which receives inside a fluid under pressure, so that the pressure causes the tube to radially expand from a position above or adjacent the opening (open position) to a size by which the reaction well opening is sealed. The radial expansion of the control line, which is positioned adjacent the opening of the reaction area, also preferably causes the tube to intrude into the reaction well and reduce its size.

To provide thermal insulation for the heat produced by the dNTP incorporation, a set of gated fluid channels orthogonal to the microfluidic channel were designed so that, on command, the microfluidic channel would be sealed by the expanding control channels to prevent heat and species diffusion. Microfluidic gates to control an existing flow channel have been used for mechanical occlusion of large, 100 μm-wide channels. Here, in contrast, they are used for both mechanical occlusion of dNTP and PPi and thermal insulation in the 5 μm-wide microfluidic channel. In modeling experiments using COMSOL Multiphysics® simulation environment (available from COMSOL Inc., Burlington Mass.), it was determined that, in a well sized at 5 μm height and width, with a bead radius of 1.4 μm, using a one control line model resulted in reaching a maximum PPi concentration in less than 0.1 seconds, as opposed to 0.25 seconds for a two control line models. Also, the temperature change was dramatically improved, showing a rises (in μK) of 1400 in less than 0.2 sec, versus change in the same amount of time in the 2-line model of only 600. Furthermore, it was determined that the temperature change is extremely sensitive to reaction volume. In creasing the reaction volume by a factor of 10 on each dimension resulted in essentially no detectable temperature change.

Figure 3A:
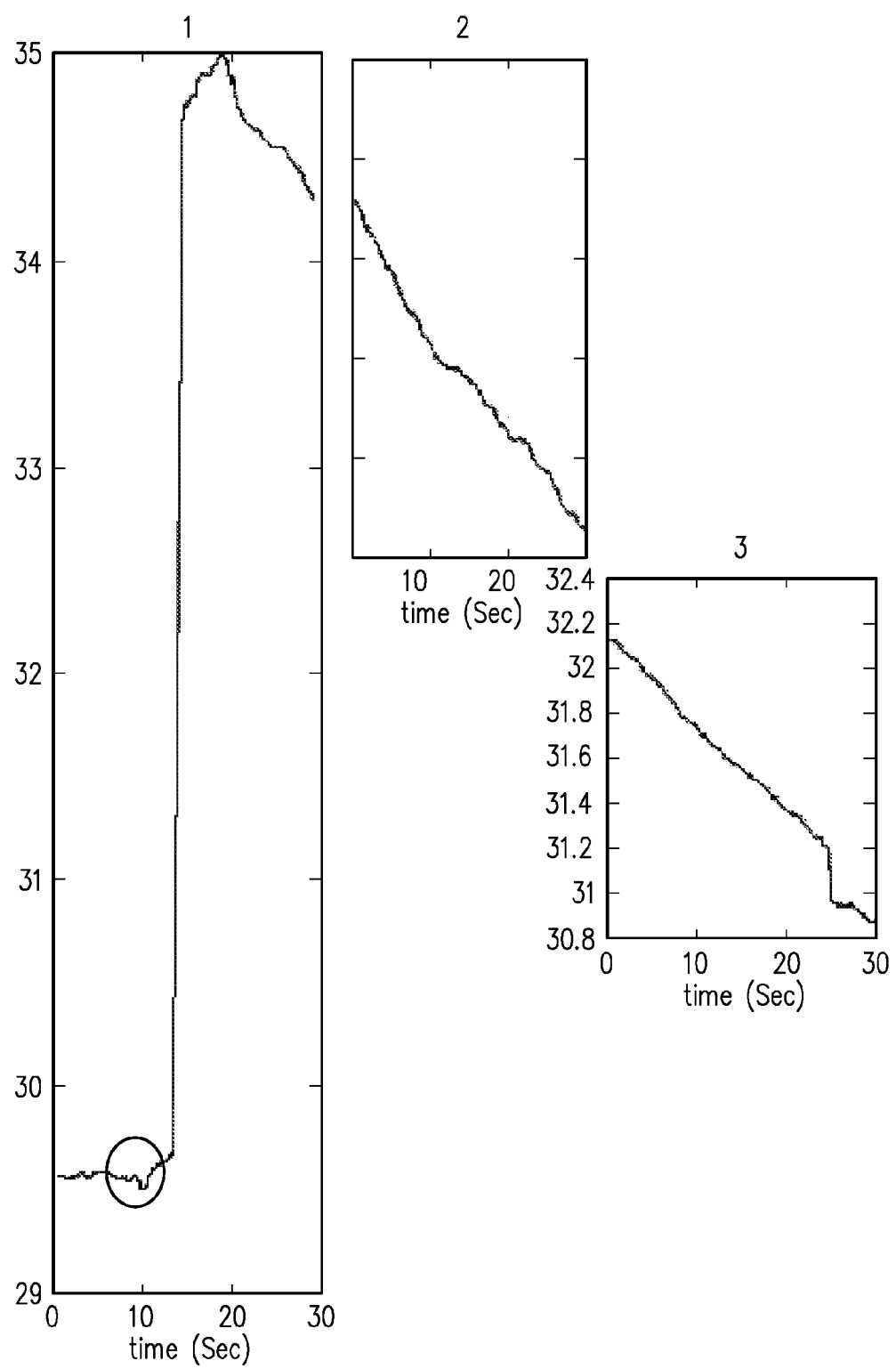
FIG. 3A-C is a series of graphs (panels 1-3 in A; 4-5 in B; noise and 6 in C) showing temperature changes plotted against ROI mean (Radiance or Temperature) measured in an IR microscope after addition of nucleotides, assembled as panels 1-5, where panel 1 shows a spike and resulting decay curve from 2, 3, 4, and 5. The panel labeled "Background noise" is an enlargement of the circled area in panel 1, showing background noise. Panel 6 is an extension of panel 5 and would be to the right of it in a single graph.
Figure 3B:
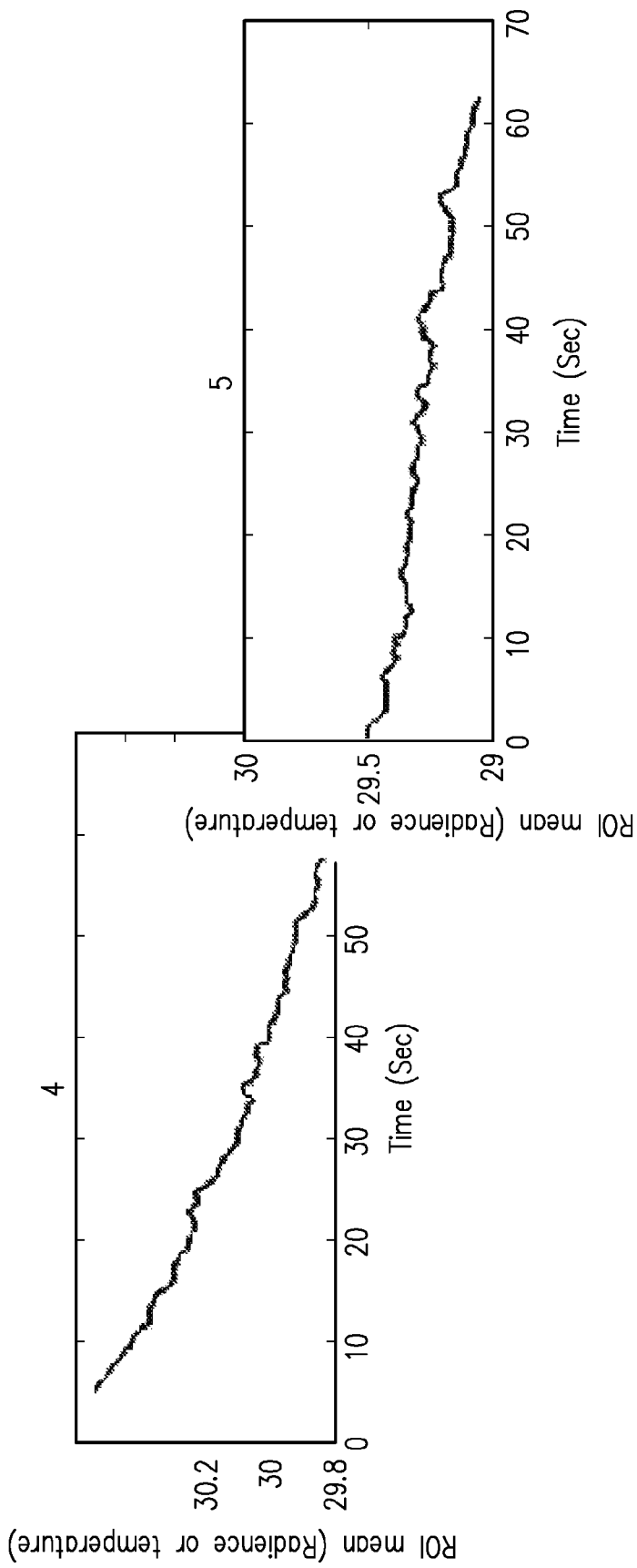
Figure 3C:
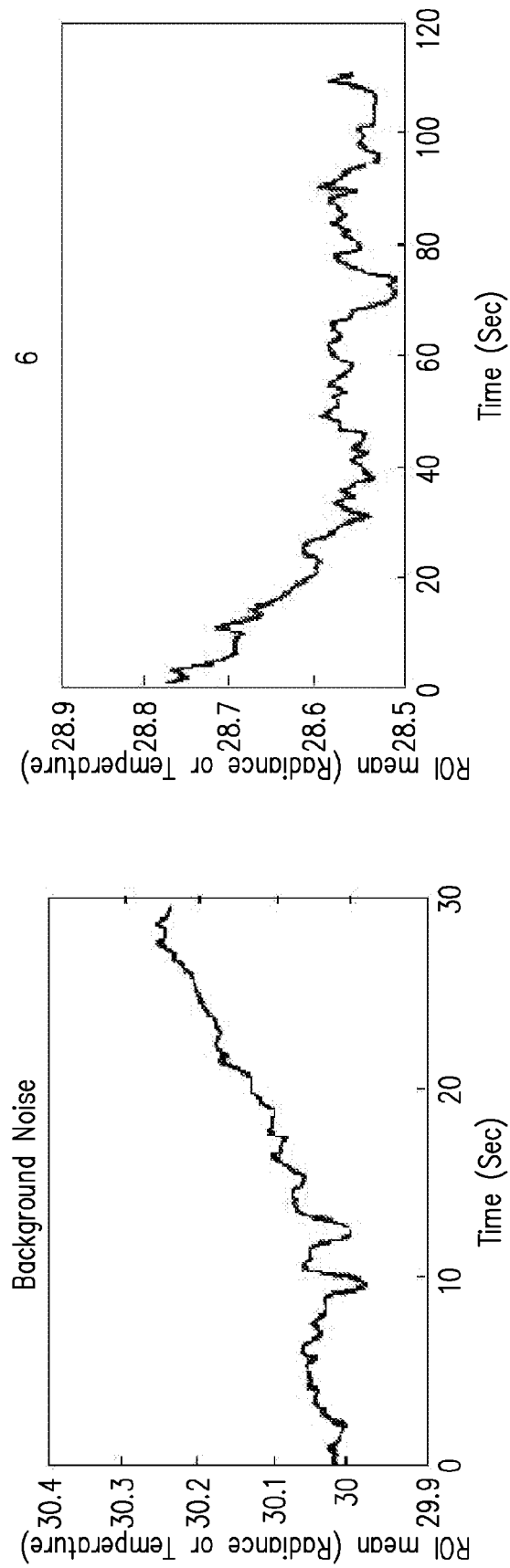

Generation of Thermal Signatures and their Measurement (FIGS. 3 and 4)

Calorimetry measures heat changes in enthalpy (DH), and is the only method that directly measures heat changes associated with intra- and intermolecular interactions.

The present device preferably employs a sensitive thermometer. In one embodiment, a resistance thermometer attached to an ASL thermometry bridge is used (See web site at aslinc.com "slash" thermometrybridges). The F18 has a Resolution of 0.003 ppm (0.75 micro K). Another embodiment uses multiple cells, one cell as a reference cell, and other cells as sample cell(s) in which the polymerase reaction takes place. Suitable instrumentation is supplied b MicroCal, LLC, which markets a VP-ITC system, which is an example of a suitable ultrasensitive isothermal titration calorimeter that uses a cell feedback network (CFB) to differentially measure and compensate for heat produced or absorbed between the sample and reference cell. Twin coin-shaped cells are mounted in a cylindrical adiabatic environment, and connect to the outside through narrow access tubes. A thermoelectric device measures the temperature difference between the two cells and a second device measures the temperature difference between the cells and the jacket. As chemical reactions occur in the sample cell, heat is generated or absorbed. The temperature difference between the sample and reference cells ($\Delta T1$) is kept at a constant value (i.e., baseline) by the addition or removal of heat to the sample cell, as appropriate, using the CFB system. The integral of the power required to maintain $\Delta T1$=constant over time is a measure of total heat resulting from the process being studied. Further details may be found in U.S. Pat. No. 5,967,659.

As described above, a sensor 14 is attached to the bottom of the well and connected by electrical leads from each reaction well. The type and shape of the sensor depends on the sensitivity of device and can include a planar, one-dimensional (thermocouple), heat detector (thermometer) or infrared (IR) sensor. Detection may be based on thin film IR-detector in the bottom of the well or a thermocouple with two adjacent nano-wires (or nano-tubes). A preferred infrared sensor is a CMOS integrated sensor. See, Ho, et al., "Sol-gel Derived Lead and Calcium Lead Titanate Pyroelectric Detectors on Si MEMS Structures," *Proceedings of the SPIE—The International Society for Optical Engineering,* 1996, vol. 2685: 91-100.

Various temperature sensors may be used. For example, U.S. Pat. No. 4,935,345 to Guilbeau, et al., issued Jun. 19, 1990, entitled "Implantable microelectronic biochemical sensor incorporating thin film thermopile," describes a biochemical sensor formed by depositing thin films of two dissimilar metals upon a substrate using microelectronic fabrication techniques. A multiplicity of thermocouple junctions are created at the intersections of the two dissimilar metal films, and the resulting series-connected thermocouple junctions are alternately designated sensing and reference junctions. Thus, the sensing junctions, but not the reference junctions, are bonded to DNA templates for initiating a chemical reaction involving the sequencing of the DNA, giving rise to a temperature differential between the sensing and reference junctions proportional to the reaction being carried out. Using materials whose conductance changes with slight temperature differences will enable measurement of nucleotide addition with a low noise voltmeter. Sensitive temperature probes can be fabricated as nanowires. See, e.g., 230. M. C. McAlpine, R. S. Friedman, S. Jin, K. Lin, W. U. Wang and C. M. Lieber, "High-Performance Nanowire Electronics and Photonics on Glass and Plastic Substrates," *Nano Lett.* 3, 1531-1535 (2003). These sensors may be integrated into MOSFET transistors, which have been fabricated to provide the above-described reaction wells and fluid channels. Two adjacent nanowires or nanotubes may be used as a thermo/pH: current meter. Detection could be based on a thin film IR-detector in the bottom of the well or a thermo/pH couple. The sensors are connected to instrumentation such as a National Semiconductor LMC6001 Ultra Ultra-Low Input Current Amplifier. The LMC6001 can provide almost noiseless amplification of high resistance signal sources, adding only 1 dB at 100 kΩ, 0.1 dB at 1 MΩ and 0.01 dB or less from 10 MΩ to 2,000 MΩ.

The instrumentation may further or alternatively comprise a sensitive pH meter, such as is described in Bashir, et al., "Micromechanical cantilever as an ultrasensitive pH microsensor," *App. Phys. Lett.* 85:3091-3093 (2002). As described there, a pH sensor with ultrahigh sensitivity was based on a microcantilever structure with a lithographically defined crosslinked copolymeric hydrogel. Silicon-on-insulator wafers were used to fabricate cantilevers on which a polymer consisting of poly (methacrylic acid) (PMAA) with polyethylene glycoldimethacrylate was patterned using freeradical UV polymerization. As the pH around the cantilever was increased above the pKa of PMAA, the polymer network expanded and resulted in a reversible change in surface stress causing the microcantilever to bend. Previous devices could measure a change in pH as low as 0.01 pH units, limited by the rms noise of 500 μV. *In* this paper, the authors report sensitivity up to $5 \times 10^{-4}$ pH. One may also use commercially available sensitive pH meters. These can measure pH changes as low as 0.001 units. They contain several inputs for indicator (ion-sensitive, redox), reference electrodes, and temperature sensors such as thermoresistors or thermocouple. The electronic pH meter uses potentiometric methods, that is, one measures a potential difference between known reference electrode and the measuring pH electrode.

Shown in FIG. 3 are data generated using IR microscopy to prove the concept for the present thermosequencing technique by measuring the heat released during the reaction of nucleotides with a template. The plot shows the result of an infrared microscopy imaging of reaction of attaching nucleotides (100 uM) to a micromolar ss-DNA (14 mM) in a run-off process (95-mer) in the active site cleft of polymerase (Klenow exo-3'); it is shown that in less than a few seconds a relatively big jump in the temperature of the media was detected after injection of the nucleotides; this result proves the principle of the present thermosequencing method. This experiment was performed with 50 uL of each of four dNTP (A, C, G, T) plus 3 uL of 14 mM DNA plus 20 uL of Polymerase (Klenow Fragment exo-, high concentration 50 U/uL) plus 200 uL of MasterMix Buffer (which included 100 mM Mg Tris Acetate 0.1M); so totally it had a volume of 423 uL. The template DNA was a 95-mer ss-DNA of $(4A5G5C5T)_5$ (SEQ ID NO: 1) which has 35-mer as hairpin (to act as a duplex primer), with the rest a ss-DNA for template-based polymerization, in which a base will be incorporated only if complementary to the template.

The trace was generated by obtaining heat measurements with a microcalorimeter (VP-ITC from Microcal LLC) and an infrared microscope (an Infrascope II from Quantum Focus Instrument Corporation), which has a temperature sensitivity of 0.1° C. (at 80° C.). The graphs have been enlarged for clarity but should be read as a single trace from the addition to an Eppindorf tube of DNA polymerase, primed template nucleotides and Mg++. The plotted ROI (range of interest) represents radiant temperature. The circled area represents noise that is shown in detail in FIG. 3C, labeled "Background noise." The panels are numbered 1-6 in the temporal order in which they were taken. They illustrate clearly the measurement of a temperature increase that would occur as a rapid spike due to the incorporation of a nucleotide. The combined decay time back to essentially zero is about 190 seconds.

Figure 4E:
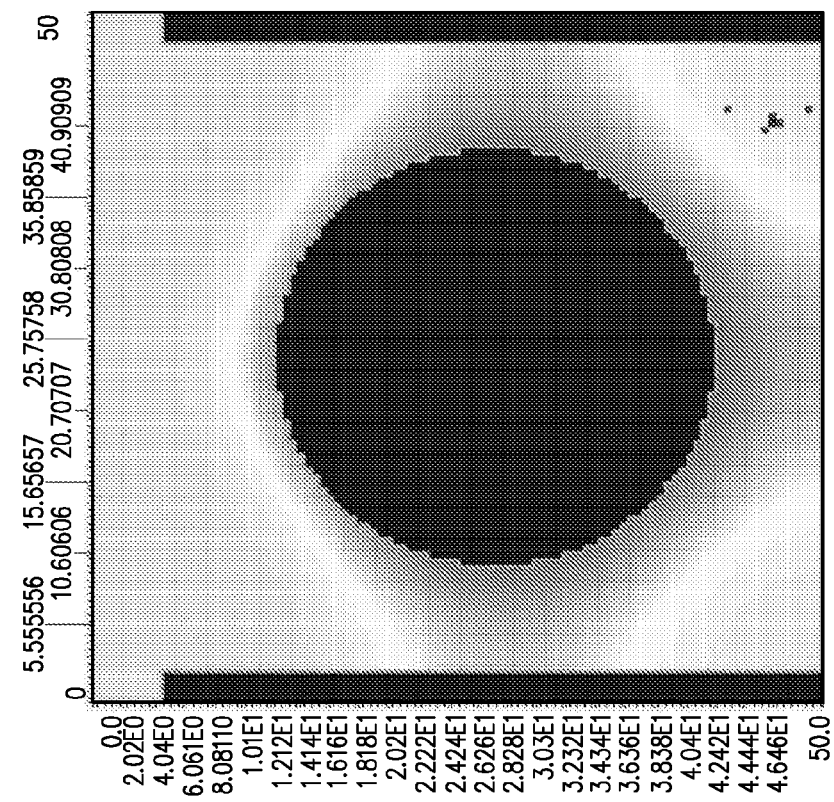

FIG. 4(A-F) illustrates a series of computer-generated images showing the heat generation profile of a bead-based microfluidic system. The program VCell was used to model a liberated heat profile as a function of time. FIGS. 4A-F show a heat generation profile of a bead-containing template DNA from 0s to 2s after addition of nucleotides. FIG. 4G shows a heat emanating from a bead inside a well that has been exposed to nucleotides. Lighter colors indicate higher heat in this figure. FIG. 4H shows a physical model of the bead and well of FIG. 4G, VCell simulations were run for different geometries, e.g., 2.8 um bead diameter, 3.5 um well diameter; 35 um bead diameter, 45 um well diameter; 1 um bead diameter, 1.3 um well diameter, to find the optimum one. The optimum bead diameter and well diameter depend on the sensor sensitivity and platform. The graphics shown in FIG. 4A-F are for a 2.8 um bead diameter and 3.5 wells. VCell was obtained from the National Resource for Cell Analysis and Modeling world wide web vcell.org/login/login.html.

Figure 5:
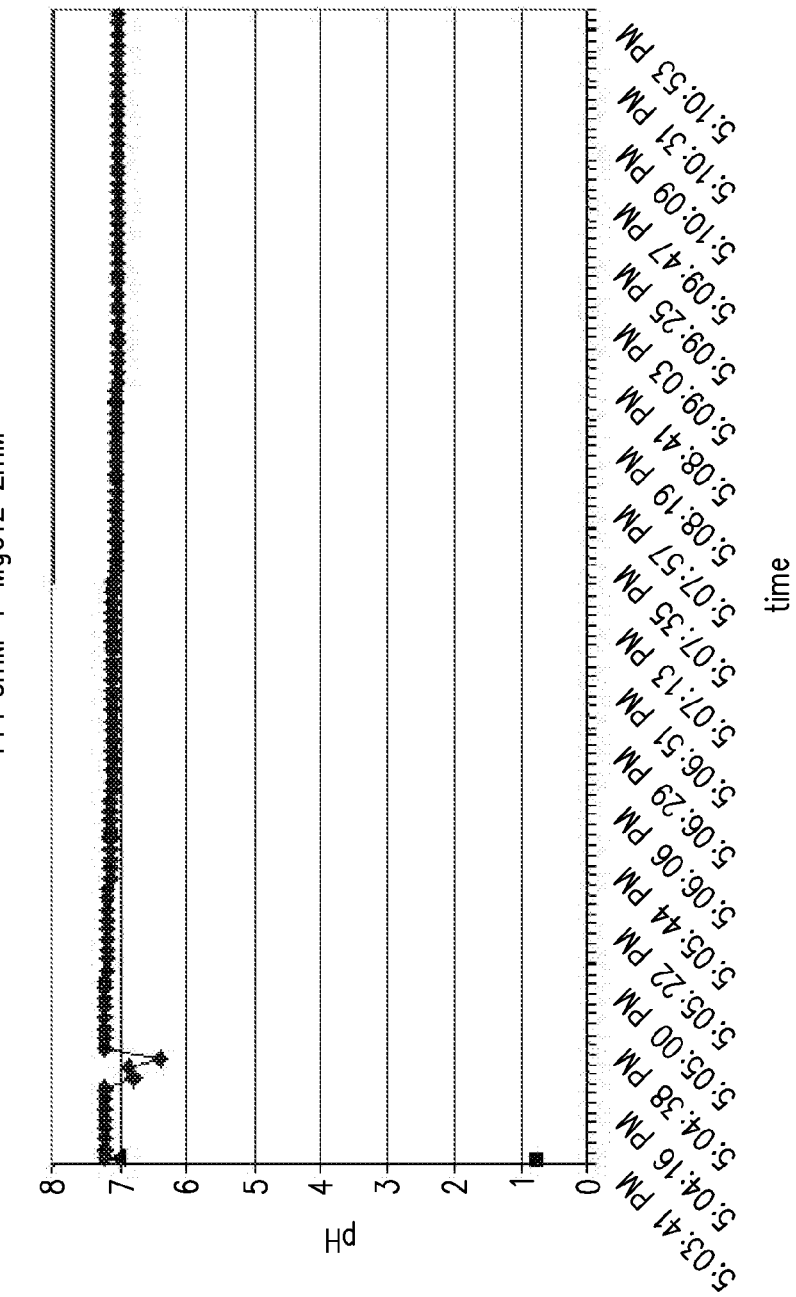
FIG. 5 is a graph of pH measurements taken over time, successfully showing the change in pH of about 0.2 from splitting PPi to 2Pi.

FIG. 5 shows experimental data obtained from measuring a pH change in 2 µM $MgCl_2$ solvent when splitting PPi to Pi. A drop of 0.2 pH was measured in 2 ml $MgCl_2$ solvent as a result of splitting PPi->2Pi in the presence of pyrophosphatase enzyme. The pH drops after adding the enzyme; after adding a few uL of the enzyme (~5 uL) to the PPi solution ($H_2PO_4$ 0.05 mM) at room temperature it can be seen that the pH was lowered after about several seconds This shows the feasibility of measuring pH changes resulting from PPi and Pi generation as a result of nucleotide incorporation.

Figure 6:
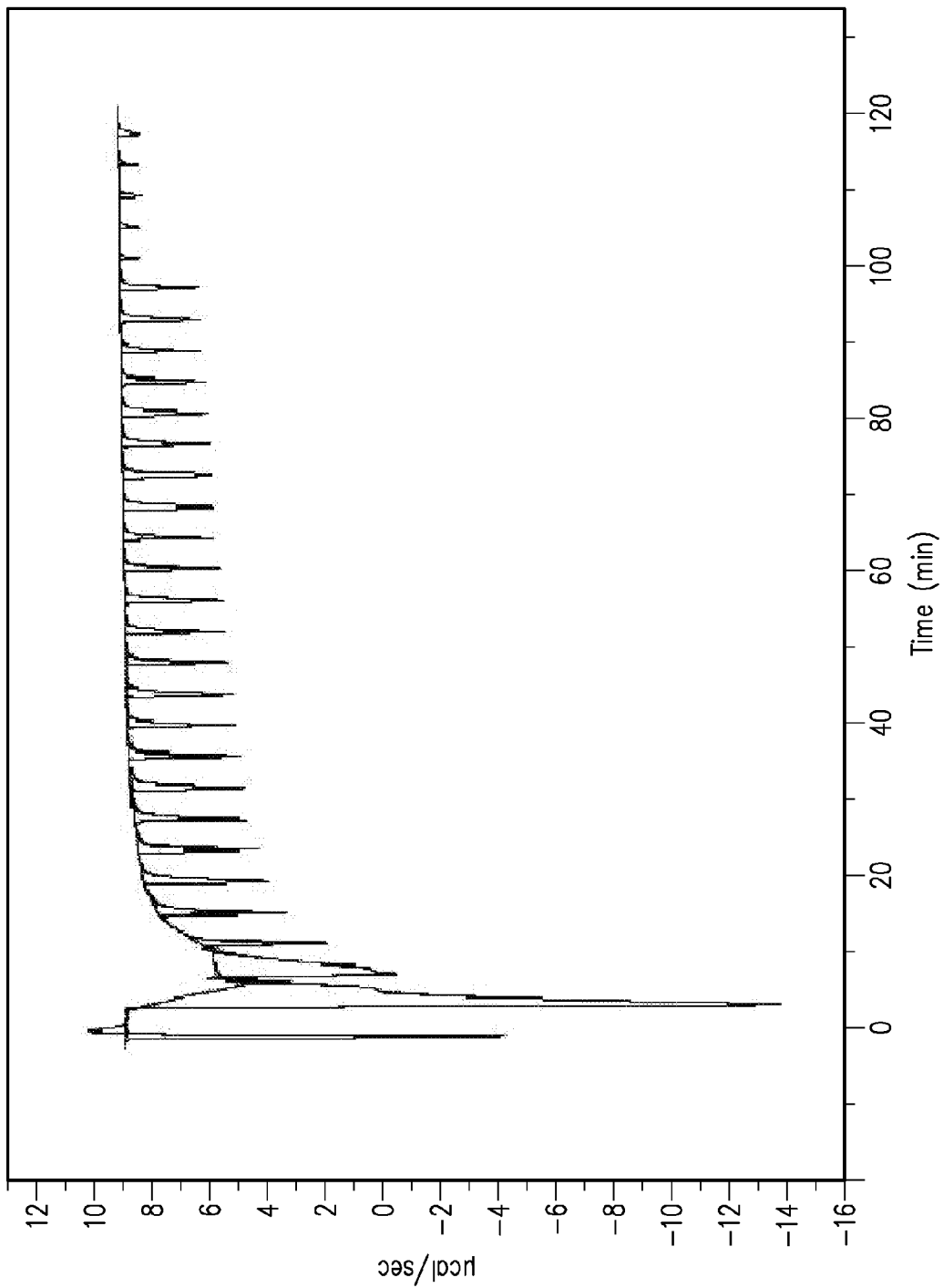
FIG. 6 is a graph of results obtained from measuring temperature increase by incorporation of nucleotides in a microcalorimeter.

FIG. 6 shows data from a Microcal instrument as discussed in connection with FIG. 3, with the being measured directly by calorimetry. The samples were prepared to contain DNA and Polymerase for the cell plus Mg 2+ buffer, dNTP and Buffer. The DNA and Polymerase was injected in the cell for 1.4 mL, and was sucked back up into the syringe to remove dNTPs after each injection. The instrument was adjusted for time intervals, vol., injection #, etc. The time interval between two injections was 240 Seconds, the syringe volume was 340 uL, and the injection duration was 20 Sec. each. Importantly, the reaction volume was limited to a cell volume of 1.4 mL.

The following conditions were employed:
CELL:
DNA: 25 uL; [DNA]=100 uM
Enzyme: 15 uL of Polymerase (5 U/uL)
Buffer (NEBuffer): 1285 uL
SYRINGE:
dNTP: 5 uL dTTP, 5 mL dCTP (100 mM)
Buffer (NEBuffer): 40 uL
10× Buffer: 280 uL As can be seen in FIG. 6, each injection resulted in a sharp peak, and the temperature returned to near baseline in about 10 minutes. This suggests that each nucleotide can be added within several minutes of the previous nucleotide without interfering with the signal (heat generation) from incorporation of a complementary nucleotide.

Further guidance in the amount of reactants and fluid volume to be used may be found in various references, such as Baillon, et al. "Continuous Microspectrophotometric Measurement of DNA Polymerase Activity: Application to the Klenow Fragment of *Escherichia coli* DNA Polymerase I and Human Immunodeficiency Virus Type 1 Reverse Transcriptase," *Proc. Nat. Acad. Sci.* 88: 1014-1018 (1991). Conditions used for the measurements in that work were incorporation of 120 pmol of dNTP in a reaction volume of 120 µl (1 µM dNTP incorporation) into a synthetic template-primer, p(dA). The transcription of poly(A)•p(dT)12-18 by reverse transcriptases was also monitored using these methods. Minetti et al. "The thermodynamics of template-directed DNA synthesis: Base insertion and extension enthalpies," *Proc. Nat. Acad. Sci.* 100: 14719-14724 (2003) also provides guidance in determining concentrations of reactants to be used with the present method. This paper teaches that heats between −9.8 and −16.0 kcal/bp for template-directed enzymatic polymerization can be found. These extension enthalpies depended on the identity of the inserting base, the primer terminus, and/or the preceding base. Heats associated with template-directed DNA synthesis were measured in a differential stopped-flow heat conduction calorimeter (Commonwealth Technology, Alexandria, Va.), The heat generated from each extension reaction was then detected by thermopiles situated on all six faces of the two mixing chambers. Integration of the area beneath the heat flow-versus-time profile determines the total heat evolved for a single extension reaction.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A method for obtaining sequence information from a single-stranded DNA template comprising:
   a) providing a primer region hybridized to the single-stranded DNA template, wherein the primer region is: (i) a hairpin formed by self-hybridization of the single-stranded DNA template, or (ii) a single-stranded oligonucleotide that is complementary to a region of the single-stranded DNA template;
   b) placing multiple copies of the single-stranded DNA template including the provided primer region in reaction chambers in a microfluidic device comprising a plurality of reaction chambers that are thermally isolated from each other, wherein the reaction chambers have a fluid volume of less than 0.1 µL of reaction mixture;
   c) adding to said reaction chambers containing said copies a mixture containing DNA polymerase and a plurality of a single species of nucleotides;
   d) removing unincorporated nucleotides;
   e) measuring a temperature change in said reaction chambers containing said copies of at least 0.003° C., said temperature change being measured by a probe in proximity to the reaction mixture as a result of the incorporation of nucleotides by the DNA polymerase producing a heat increase indicative of the incorporation of a complementary nucleotide into the primer region hybridized to the single-stranded DNA template; and
   f) repeating steps c), d), and e) to obtain the sequence information.

2. The method of claim 1, further comprising immobilizing the single-stranded DNA template.

3. The method of claim 2, wherein the immobilizing comprises immobilizing the single-stranded DNA template on a bead, which has a diameter at least half of the diameter of an opening in the reaction chamber.

4. The method of claim 3, wherein the bead is made of metal.

5. The method of claim 3 wherein the bead is a magnetic bead approximately 2-3 µm in diameter.

6. The method of claim 1, wherein the measuring of the temperature change is accomplished using a heat sensor.

7. The method of claim 6 wherein the heat sensor is selected from the group consisting of a picocalorimeter, a planar one-dimensional thermocouple, a thermometer, and an infrared (IR) sensor.

8. The method of claim 6 wherein the heat sensor is a planar sensor on a bottom surface of the reaction chamber.

9. The method of claim 6 wherein the heat sensor is a thermocouple extending into a bottom portion of the reaction chamber.

10. The method of claim 6 wherein the heat sensor is an IR detector in an IR microscope.

11. The method of claim 1 further comprising the step of measuring a change in pH of about 0.001 units, said change in pH comprising a drop in pH that indicates the incorporation of a nucleotide complementary to the single-stranded DNA template into the primer.

12. The method of claim 1, wherein different reaction chambers in the plurality of thermally isolated reaction chambers contained in the microfluidic device contain primer regions hybridized to single-stranded DNA templates that differ in sequence between reaction chambers.

13. The method of claim 12 wherein the plurality of reaction chambers is contained in a single polymeric substrate provided with fluid channels.

14. The method of claim 1 wherein the primer region comprises a single-stranded oligonucleotide that is complementary to a region of the single-stranded DNA template.

15. The method of claim 1 wherein the reaction mixture is between about 70 picoliters and about 30 femtoliters in volume.

16. The method of claim 1 wherein said multiple copies of the single-stranded DNA template in a reaction chamber comprise at least $10^3$ copies.

17. The method of claim 1 wherein the sequence information comprises 80 to 120 bases.

18. The method of claim 11 further comprising the step of splitting pyrophosphate (PPi) to 2Pi.

\* \* \* \* \*

UNITED STATES PATENT AND TRADEMARK OFFICE
CERTIFICATE OF CORRECTION

| | | |
|---|---|---|
| PATENT NO. | : 7,932,034 B2 | Page 1 of 1 |
| APPLICATION NO. | : 11/959317 | |
| DATED | : April 26, 2011 | |
| INVENTOR(S) | : Esfandyarpour et al. | |

It is certified that error appears in the above-identified patent and that said Letters Patent is hereby corrected as shown below:

In the Specification Under Column 1:

• Please replace Column 1, line no. 11-15 with:

-- FEDERALLY-SPONSORED RESEARCH OR DEVELOPMENT
This invention was made with Government support under contract HG003571 awarded by the National Institutes of Health. The Government has certain rights in this invention. --

Signed and Sealed this
Ninth Day of April, 2013

Teresa Stanek Rea
*Acting Director of the United States Patent and Trademark Office*

SEQUENCE LISTING

```
<160> NUMBER OF SEQ ID NOS: 2

<210> SEQ ID NO 1
<211> LENGTH: 95
<212> TYPE: DNA
<213> ORGANISM: Artificial Sequence
<220> FEATURE:
<223> OTHER INFORMATION: template DNA

<400> SEQUENCE: 1 aaaaggggc ccccttttta aaggggggcc cccttttaa aaggggccc ccttttaaa      60 aggggcccc cttttaaaa gggggccccc ttttt                              95

<210> SEQ ID NO 2
<211> LENGTH: 34
<212> TYPE: DNA
<213> ORGANISM: artificial
<220> FEATURE:
<223> OTHER INFORMATION: synthetic

<400> SEQUENCE: 2
atgcattgca tgcaatgcat gcatgcatgc atgc                             34
```